United States Patent
Rotello et al.

(10) Patent No.: US 10,073,340 B2
(45) Date of Patent: Sep. 11, 2018

(54) PROTEIN FILMS AND METHODS OF FORMING THE SAME

(71) Applicant: University of Massachusetts, Boston, MA (US)

(72) Inventors: Vincent M Rotello, Amherst, MA (US); Bradley Duncan, Boston, MA (US); Li-Sheng Wang, Boston, MA (US); Eunhee Jeoung, Boston, MA (US); Chandramouleeswaran Subramani, Boston, MA (US); Krishnendu Saha, Boston, MA (US)

(73) Assignee: University of Massachusetts, Boston, MA (US)

( * ) Notice: Subject to any disclaimer, the term of this patent is extended or adjusted under 35 U.S.C. 154(b) by 48 days.

(21) Appl. No.: 14/873,540

(22) Filed: Oct. 2, 2015

(65) Prior Publication Data

US 2016/0096935 A1 Apr. 7, 2016

Related U.S. Application Data (60) Provisional application No. 62/059,024, filed on Oct. 2, 2014.

(51) Int. Cl.
*C08J 5/18* (2006.01)
*C12N 11/02* (2006.01)
*G03F 7/00* (2006.01)
*C12N 11/14* (2006.01)

(52) U.S. Cl.
CPC ............ *G03F 7/0002* (2013.01); *C12N 11/14* (2013.01)

(58) Field of Classification Search
None
See application file for complete search history.

(56) References Cited

U.S. PATENT DOCUMENTS

| | | | | |
|---|---|---|---|---|
| 4,103,064 A | * | 7/1978 | McAlear | B82Y 10/00 174/126.1 |
| 2001/0006706 A1 | * | 7/2001 | Picard | B01D 69/122 427/350 |
| 2009/0264317 A1 | * | 10/2009 | Ofir | B82Y 10/00 506/16 |
| 2012/0034291 A1 | * | 2/2012 | Amsden | B82Y 10/00 424/443 |
| 2013/0325121 A1 | * | 12/2013 | Whatley | A61F 2/18 623/10 |

OTHER PUBLICATIONS

Bertotalus et al. "Glomerular sieving of anionic and neutral bovine albumins in proteinuric rats", Kidney International 28: 467-476, 1985.*
James et al. "Patterned protein layers on solid substrates by thin stamp microcontact printing", Langmuir 14: 741-744, 1998.*
Zink et al. "Physical, chemical, and biochemical modifications of protein-based films and coatings: and extensive review", International Journal of Molecular Sciences 17: 1376-, 2016.*
Ciannamea et al. "Physical and mechanical properties of compression molded and solution casting soybean protein concentrate based films", Food Hydrocolloids 38 (38): 193-204, 2014.*
Cho et al. "Properties of wheat gluten/poly (lactic acid) laminates", Journal of Agricultural and Food Chemistry 58(12): 7344-7350, 2010.*
Hamman et al. "Determination and quantification of molecular interactions in protein films: a review", Materials 7: 7975-7996, 2014.*
Howitt "Silk Fibroin as a Fibrous Protein1." Textile Research Journal 25(3): 242-246, 1955 (Year: 1995).*
Hsu, Bryan B, et al., "Ordered and Kinetically Discrete Sequential Protein Release from Biodegradable Thin Films", Angew. Chem. Int. Ed. 53, (2014), 8093-8098.
Kim, Sunghwan, et al., "All-water-based electron-beam lithography using silk as a resist", Nature Nanotechnology Letters, (Mar. 2014), 1-5.
Perry, Hannah, et al., "Nano- and Micropatterning of Optically Transparent Mechanically Robust, Biocompatible Silk Fibroin Films", Adv. Mater. 20, (2008), 3070-3072.

* cited by examiner

*Primary Examiner* — Emily A Cordas
(74) *Attorney, Agent, or Firm* — Schwegman Lundberg & Woessner, P.A.

(57) ABSTRACT

Various embodiments disclosed relate to protein films and methods of making the same. In various embodiments, the present invention provides a method of making a protein film including placing on a substrate a protein solution, to form a precursor protein film. The protein solution includes one or more proteins. The method includes compressing the precursor protein film to form a protein film.

16 Claims, 8 Drawing Sheets

PROTEIN FILMS AND METHODS OF FORMING THE SAME

CROSS-REFERENCE TO RELATED APPLICATION

This application claims the benefit of priority to U.S. Provisional Patent Application Ser. No. 62/059,024, filed Oct. 2, 2014, the disclosure of which is incorporated herein in its entirety by reference.

STATEMENT OF GOVERNMENT SUPPORT

This invention was made with Government support under CHE-1307021 and CMMI-1025020 awarded by the National Science Foundation. The U.S. Government has certain rights in this invention.

BACKGROUND

Anti-fouling and anti-microbial surfaces can be useful in a wide-variety of applications, including in medical devices and on surfaces used in marine environments. However, anti-fouling and anti-microbial surfaces can be both difficult and expensive to form.

SUMMARY OF THE INVENTION

Various embodiments of the present invention provide a method of making a protein film. The method includes placing on a substrate a protein solution, to form a precursor protein film. The protein solution includes one or more proteins. The method includes compressing the precursor protein film, to form a protein film.

Various embodiments of the present invention provide a protein film. The protein film includes one or more proteins that at least partially retain their secondary structure in the film. The protein film includes intermolecular hydrophobic interactions between the proteins.

Various embodiments of the present invention have advantages over other protein films and methods for making the same, at least some of which are unexpected. In various embodiments, the method and the protein film are versatile with respect to protein building block. In various embodiments, the method of making the protein film can avoid environmentally hazardous materials during the fabrication process such as organic solvents or chemical crosslinkers. In various embodiments, the deposition of the protein onto the substrate and the formation thereof into a protein film is facile and versatile. In various embodiments, the method can provide protein films on three-dimensional surfaces. In various embodiments, the method can include deposition methods that give additional patterning control, or that allow production of multicomponent protein films. In various embodiments, a wide variety of substrate materials can be used.

In various embodiments, the proteins in the film can at least partially retain their native structure, for example, secondary structure. In various embodiments, the stability and biodegradability of the protein film can be easily controlled. In various embodiments, the porosity of the protein film can be easily controlled, such as via addition of porogens to the film; such porous protein films can be used as biomembranes for controlled diffusion. In various embodiments, the protein film can have nanoscale features and patterns. In various embodiments, the protein film can include a non-fouling surface. For example, in some embodiments, the surface of the protein film can prevent macromolecule (e.g., protein) adsorption. In various embodiments, the resistance to macromolecule adsorption can make the protein film useful for coating implantable biomedical devices or for using as a surface treatment for marine equipment. In various embodiments, cellular adhesion can be easily regulated by using an appropriate protein. In various embodiments, the protein film can direct cellular growth in a nanoscale architecture. In various embodiments, the protein film can have favorable biocompatibility. In various embodiments, the protein film can have tissue engineering applications.

In various embodiments, small molecules can be incorporated into the protein film (e.g., antibiotics, halide ions such as chloride ions), augmenting functional behavior of the film. In various embodiments, the film can be used for controlled-release or delayed release of a small molecule incorporated into the film. In various embodiments, with appropriate loading of secondary components, or by chlorination of the proteins in the film (e.g., via amine groups), the protein film can be used as an antimicrobial surface coating agent (e.g., for catheters or other indwelling devices). In various embodiments, the protein film can respond rapidly to humidity changes (e.g., via color change). In various embodiments, the protein film can act as a matrix for controlled growth of nanoparticles.

BRIEF DESCRIPTION OF THE FIGURES

The drawings illustrate generally, by way of example, but not by way of limitation, various embodiments discussed in the present document.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001."

In the methods of manufacturing described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "solvent" as used herein refers to a liquid that can dissolve a solid, liquid, or gas. Nonlimiting examples of solvents are silicones, organic compounds, water, alcohols, ionic liquids, and supercritical fluids.

As used herein, the term "polymer" refers to a molecule having at least one repeating unit and can include copolymers.

Method of Making a Protein Film.

In various embodiments, the present invention provides a method of making a protein film. The method can include placing on a substrate a protein solution, to form a precursor protein film. The protein solution includes one or more proteins. The method can include compressing the precursor protein film, to form a protein film.

The method can be a scalable, additive-free nanoimprint lithography-based method for the fabrication of stable, patterned protein films. Through parametric variation of temperature and pressure the stability and biodegradability of the protein film can be controlled. By incorporating small molecules into the precursor film prior to nanoimprinting, the functional behavior of the protein film can be augmented. Various embodiments of the film can have antimicrobial surfaces, such as those include antimicrobial materials.

The placing of the protein solution on the substrate to form the precursor protein film can be any suitable placing. The placing can include printing, dipping, brushing, soaking, immersion, spraying, spin casting, or a combination thereof. For example, the placing can include at least one of offset printing, screen printing, flexographic printing, inkjet printing, laser printing, dot matrix printing, daisy wheel printing, pad printing, relief printing, rotogravure printing, gravure printing, jet printing, ultrasonic spray printing, piezoelectric printing, spin casting, and three dimensional (3D) printing. In some embodiments, the placing includes spin casting. The placing can include evaporating or otherwise removing any suitable proportion of any one or more solvents from the protein solution to form the precursor protein film.

The protein solution can include any one or more suitable proteins. The protein solution can be an aqueous protein solution. The one or more proteins can be any suitable proportion of the protein solution, such as about 0.01 wt % to about 99.9 wt %, about 1 wt % to about 20 wt %, about 5 wt % to about 15 wt %, or about 0.01 wt % or less, or less than, equal to, or more than about 0.1 wt %, 1, 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, 65, 70, 75, 80, 85, 90, 95, 96, 97, 98, 99, 99.9, or about 99.99 wt % or more. The protein solution can include at least one of fibrous protein (e.g. cytoskeletal protein, extracellular matrix protein), a globular protein (e.g., plasma protein, coagulation factor, acute phase protein, hemoprotein, cell adhesion protein), a transmembrane transport protein (e.g., ion-pumping enzyme, ion channel protein, synport or antiport protein), a hormone or growth factor protein, a receptor protein, a DNA-binding protein, a transcription regulation protein, an immune system protein, a nutrient storage or transport protein, a chaperone protein, and an enzyme. In various embodiments, the protein solution includes at least one of anionic bovine serum albumin, neutral hemoglobin, and cationic lysozyme. In some embodiments, the protein solution can be substantially additive-free. In some embodiments, the protein solution can include one or more additional suitable components.

The substrate can be any suitable substrate, such that the method can be carried out as described herein. The substrate can be stiff or flexible. The substrate can be a plasma-cleaned substrate. In some examples, the substrate can include at least one of a silica wafer, glass, quartz, a polydimethylsiloxane, and a polyester (e.g., MYLAR®). In various embodiments, the substrate can be cleaned prior to placing the protein solution there, such as via plasma-cleaning.

The precursor protein film can have any suitable thickness. In some embodiments. The precursor protein film can have a thickness of about 1 nm to about 100 microns, or about 100 nm to about 300 nm, or about 1 nm or less, or less than, equal to, or more than about 2 nm, 3, 4, 5, 10, 20, 25, 50, 100, 125, 150, 175, 200, 225, 250, 275, 500, 750 nm, 1 micron, 2, 3, 4, 5, 10, 20, 25, 50, 75, or about 100 microns or more.

The compressing of the precursor protein film to form the protein film can be any suitable compressing, such that the method can be carried out as described herein. The compressing can bring the one or more proteins in the precursor protein film into a suitable arrangement (e.g., including intermolecular hydrophobic interactions between the proteins) such that an embodiment of the protein film described herein is formed. In some embodiments, the compressing can increase the proximity of the one or more proteins to one another. In some embodiments, the concentration of solvent in the formed protein film can be the same as the concentration of solvent in the precursor protein film. In some embodiments, the compressing can decrease the concentration of solvent (e.g., increase the concentration of the one or more proteins in the protein film compared to the precursor protein film).

The compressing can be carried out via compression from surrounding gases, such as by placing the protein film under a pressurized environment. The compressing can be carried out via compression from a physical object, such as a mold or a press. The compressing can be carried out using a combination of a pressurized environment and compression from a physical object. The compressing of the precursor film can be carried out at any suitable temperature, such as about −50° C. to about 500° C., about 50° C. to about 250° C., about 140° C. to about 200° C., or about −50° C. or less, or less than, equal to, or more than about −40° C., −30, −20, −10, −5, 0, 5, 10, 15, 20, 25, 30, 35, 40, 45, 50, 60, 70, 80, 90, 100, 105, 110, 115, 120, 125, 130, 135, 140, 145, 150, 155, 160, 165, 170, 175, 180, 185, 190, 195, 200, 210, 220, 230, 240, 250, 275, 300, 400, or about 500° C. or more. The compressing of the precursor film can be carried out using any suitable pressure (e.g., the pressure between the mold and the pressed precursor film), such as about 14 psi to about 20,000 psi, about 200 psi to about 800 psi, about 14 psi or less, or less than, equal to, or more than about 20 psi, 25, 30, 35, 40, 45, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 650, 700, 750, 800, 900, 1,000, 1,500, 2,000, 2,500, 5,000, 10,000, 15,000, or about 20,000 psi or more. In various embodiments, compressing of the precursor film forms a pattern in the film. Compressing of the precursor film can form one or more nanoscale features (e.g., 1 nm to about 100 nm) in the protein film.

In some embodiments, the compressing can include placing the precursor protein film in a pressurized environment, such that pressure from surrounding gases compresses the precursor protein film. In some examples, the pressurized environment can be provided by a pressure vessel (e.g., a pressurized vessel), such as a pressure reactor. The pressure vessel can be any suitable pressure vessel. A pressure vessel can includes a means for injecting gas therein (e.g., a valve connected to a gas source) and for controlling the pressure of the gas in the interior of the vessel (e.g., the valve can be adjustable, and a pressure gauge can be provided). In some embodiments, the pressure vessel can also include a heating source that allows the interior of the pressure vessel to attain a desired temperature.

In some embodiments, the compressing of the precursor protein film to form the protein film can include pressing the precursor protein film, such as with a mold. The mold can be made of any suitable material, such that the method can be carried out as described herein. In some embodiments, the mold can be a silane-functionalized or a siloxane mold, such as a fluorosilane-functionalized mold or a polydimethylsiloxane mold. Pressing the precursor film with the mold can be carried out in any suitable way. In some embodiments, pressing of the precursor film with the mold can include at least one of imprinting and embossing. Pressing the precursor film with a mold can include nanoimprint lithography (NIL), such as patterned nanoimprint lithography.

The method can further include washing the protein film, such as using an aqueous solution or an organic solvent.

The method can further include at least partially removing the protein film from the substrate, such as about 0.01% to about 100% of the surface area of one side of the protein film, such as about 0.01% or less, or less than, equal to, or more than about 0.1%, 1, 2, 3, 5, 10, 15, 20, 25, 30, 40, 50, 60, 70, 80, 90, 95, 96, 97, 98, 99, or about 100% of the surface area of one side of the protein film.

In various embodiments, the method includes growing cells on the protein film. The cells can be any suitable one or more cells, and the growing can be conducted in any suitable fashion. In some embodiments, the cells grown on the protein film substantially align with a pattern in the protein film, such as a pattern formed by the compressing of the precursor film (e.g., such as a pattern formed by the pressing of a mold on the precursor film or via other compressing techniques).

The protein film can be substantially water-stable, such that under aqueous conditions little to no degradation or dissolution of the protein film occurs. In some embodiments, the protein film can be substantially resistant to hydrolysis, such as when the compressing is performed at temperatures greater than about 150° C., 155, 160, 165, 170, 175, 180, 185, 190, or greater than about 200° C. In some embodiments, the protein film can be degradable, such that hydrolysis occurs under physiological conditions. The protein solution can include one or more components (e.g., small molecules such as antibiotics) designed to the released into a physiological system upon degradation of the protein film, such in a controlled-release or delayed-release manner. In some embodiments, a degradable film can be formed from a method that includes performing the compressing of the precursor protein film at less than (e.g., not exceeding) about 200° C., or less than about 195° C., 180, 175, 170, 165, 150, 155, 150, 145, 140, 135, 130° C., or less than about 125° C.

Various physical properties of the precursor proteins can be retained in the protein film. For example, the structure (e.g., the secondary structure) of one or more of the precursor proteins can be substantially retained. In some embodiments, the surface of the protein film can include one or more charges that correspond to charges from the proteins in the protein film.

The protein film can be substantially water-stable, such that under aqueous conditions little to no degradation or dissolution of the protein film occurs. In some embodiments, the protein film can be degradable, such that hydrolysis occurs under physiological conditions. The protein solution can include one or more components (e.g., small molecules such as antibiotics) designed to the released into a physiological system upon degradation of the protein film, such in a controlled-release or delayed-release manner.

Protein Film.

Various embodiments of the present invention provide a protein film. The protein film can be any suitable protein film that can be or that is formed by any embodiment of the method of making a protein film described herein. In various embodiments, the protein film includes one or more proteins that at least partially retain their secondary structure in the protein film, wherein the protein film includes intermolecular hydrophobic interactions between the proteins.

The protein film can have any suitable thickness. In various embodiments, the protein film can have a thickness of about 1 nm to about 100 microns, or about 100 nm to about 300 nm, or about 1 nm or less, or less than, equal to, or more than about 2 nm, 3, 4, 5, 10, 20, 25, 50, 100, 125, 150, 175, 200, 225, 250, 275, 500, 750 nm, 1 micron, 2, 3, 4, 5, 10, 20, 25, 50, 75, or about 100 microns or more.

The protein film can be substantially biocompatible, such that the protein film can be safely come into contact with internal tissues for long periods such as on an implant surface.

The protein film can be substantially resistant to degradation in a solution including serum, such as any suitable serum at any suitable concentration.

The protein film can be substantially resistant to macromolecule adsorption, such as protein adsorption. The protein film can be substantially resistant to protein fouling.

In various embodiments, the protein film can include cells thereon. The cells can be substantially aligned with a pattern on the protein film.

In various embodiments, the protein film can respond to humidity changes rapidly, such as by changing color. Various embodiments provide a moisture-sensing patch including the protein film.

The protein film can have any suitable porosity.

Various embodiments provide a catheter coating, or other medical implant coating, including the protein film.

EXAMPLES

Various embodiments of the present invention can be better understood by reference to the following Examples which are offered by way of illustration. The present invention is not limited to the Examples given herein.

General.

Materials:

BSA, Hemo, and Lyso were purchased from Fisher Scientific and used without further purification. Silica wafers were purchased from WRS Materials. Quartz microscopy slides were purchased from Electron Microscopy Sciences. MILLI-Q® water was purified using a Millipore water purification system.

Film Preparation:

10% w/w solutions of protein in MILLI-Q® water were filtered using a 0.22 µm filter and spin casted at 3000 rpm for 60 s onto an oxygen plasma cleaned silicon substrate, yielding a thin film of protein.

Nanoimprint Lithography (NIL):

Nanoimprinting of protein films was performed using a Nanonex NX-2000 nanoimprintor with silicon molds. Imprinting was performed at various temperatures and pressures for 5 min. A silicon NIL mold (line width 303 nm, period 606 nm, and groove depth 190 nm) from Lightsmyth Technologies was used in the cell patterning. All molds were treated with heptadecafluoro-1,1,2,2-(tetrahydrodecyl)dimethyl-chlorosilane at 75° C. for 2 days in a vacuum chamber.

Cell Culture:

Mouse fibroblast cells 3T3 (ATCC CRL-1658) were cultured in Dulbecco's Modified Eagle's Medium (ATCC 30-2002) supplemented with 10% bovine calf serum (ATCC 30-2030) and 1% antibiotics in T75 flasks. Cells were maintained at 37° C. in a humidified atmosphere of 5% $CO_2$ and were sub-cultured once in 4 days.

Cell Adhesion:

3T3 cells grown in T75 flasks were washed with phosphate buffered saline (PBS), trypsinized with 1X trypsin and collected in DMEM media. Cells were centrifuged and were re-suspended in fresh DMEM media and counted using a hemocytometer. Protein film coated surfaces were placed in a 6-well plate where 3T3 cells were added to each well (100000 cells/well) and incubated for 48 h at 37° C. in a humidified atmosphere of 5% $CO_2$. Following incubation, cells were washed with PBS three times and incubated with Calcein AM (Biotium Inc, 80011-2) and propidium iodide (Invitrogen) in PBS (final concentration 3 µM each) for 30 min. Fluorescence microscopy images were taken using an OLYMPUS® IX51 microscope to visualize the adhered live (Calcein AM stained, green) and dead cell (PI stained, red) population in each surface.

Cell Alignment on Nano-Patterned Surfaces:

The cell alignment on the patterned surfaces were performed according to previously published procedures. Briefly, 100000 cells were incubated with the nano-patterned surface for 48 h and washed twice with pre-warmed PBS and fixed with 3.7% methanol-free formaldehyde solution (Electron Microscopy Sciences 15714-S). Cells were then washed three times with PBS and extracted with 0.1% Triton X-100 in PBS for 5 min. Surfaces were then washed with PBS and incubated with a solution of Oregon Green 488 phalloidin (Invitrogen 07466) to stain actin filaments and Hoechst nuclear stain (Invitrogen H1399) at final concentrations of 200 nM and 1 µg/mL respectively in PBS. After 30 minutes, the cells were washed three times and the images were captured using a confocal microscope (Olympus). Cell alignment was measured using ImageJ software by determining the angle of the long axis of the nucleus with respect to the parallel direction of the pattern. 45 random cells from each image were counted according to their angle of alignment from 0° to 90° in 10° increments and their % distribution was graphed.

Characterization:

Bright field images and fluorescence were detected using an OLYMPUS® IX51 microscope with excitation wavelengths of 470 nm and 535 nm. AFM imaging of the surfaces was done on a Dimensions 3000 (Veeco) in tapping mode using a RTESP7 tip (Veeco). Confocal images were obtained using a Zeiss LSM 510 Meta microscope. The film thickness of the protein films was measured by a Rudolph Research Auto EL ellipsometer. Far-UV circular dichroism (CD) spectra were measured on a JASCO® J-720 spectropolarimeter with a quartz cuvette of 1 mm path length at 25° C. The spectra were recorded from 200 to 260 nm as an average of three scans at a rate of 20 nm/min.

Protein-derived materials provide an inherently bio compatible and sustainable platform for the generation of functional materials. Resistance to aqueous degradation of protein films is crucial for most applications. Current methods to produce stable protein films are limited to two main strategies: using the limited variety of naturally self-assembling proteins or using crosslinkers. While the crosslinking strategy generates functionally diverse structures, unreacted additives retained in crosslinked protein films adversely affect the final behavior. A scalable, additive-free nanoimprint lithography (NIL) based method is demonstrated for the fabrication of stable, patterned protein films. This approach is general in terms of protein building block with the imprinted proteins retaining much of their native structure after the imprinting process. Through parametric variation of temperature and pressure stability and biodegradability of the films can be controlled. The utility of these films as biomaterials is demonstrated through the generation of non-fouling surfaces and regulation of cellular adhesion through choice of protein precursor.

Proteins are attractive precursors for the manufacturing of functional surfaces due to their intrinsic structural and functional diversity, making them highly versatile building blocks for generating materials featuring a wide range of properties. Proteins also feature aqueous processability and have minimal environmental impact, making them sustainable "green" materials. Three proteins were chosen featuring widely differing size and charge to highlight building block diversity and concomitant control of materials properties. These readily available proteins were: anionic bovine serum albumin (BSA, MW 66.3 kDa, pI 4.8), neutral hemoglobin (Hemo, MW 64.5 kDa, pI 6.8), and cationic lysozyme (Lyso, MW 14.3 kDa, pI 11).

Example 1. Preparation and Imprinting/Embossing of Precursor Protein Films

Figure 1:
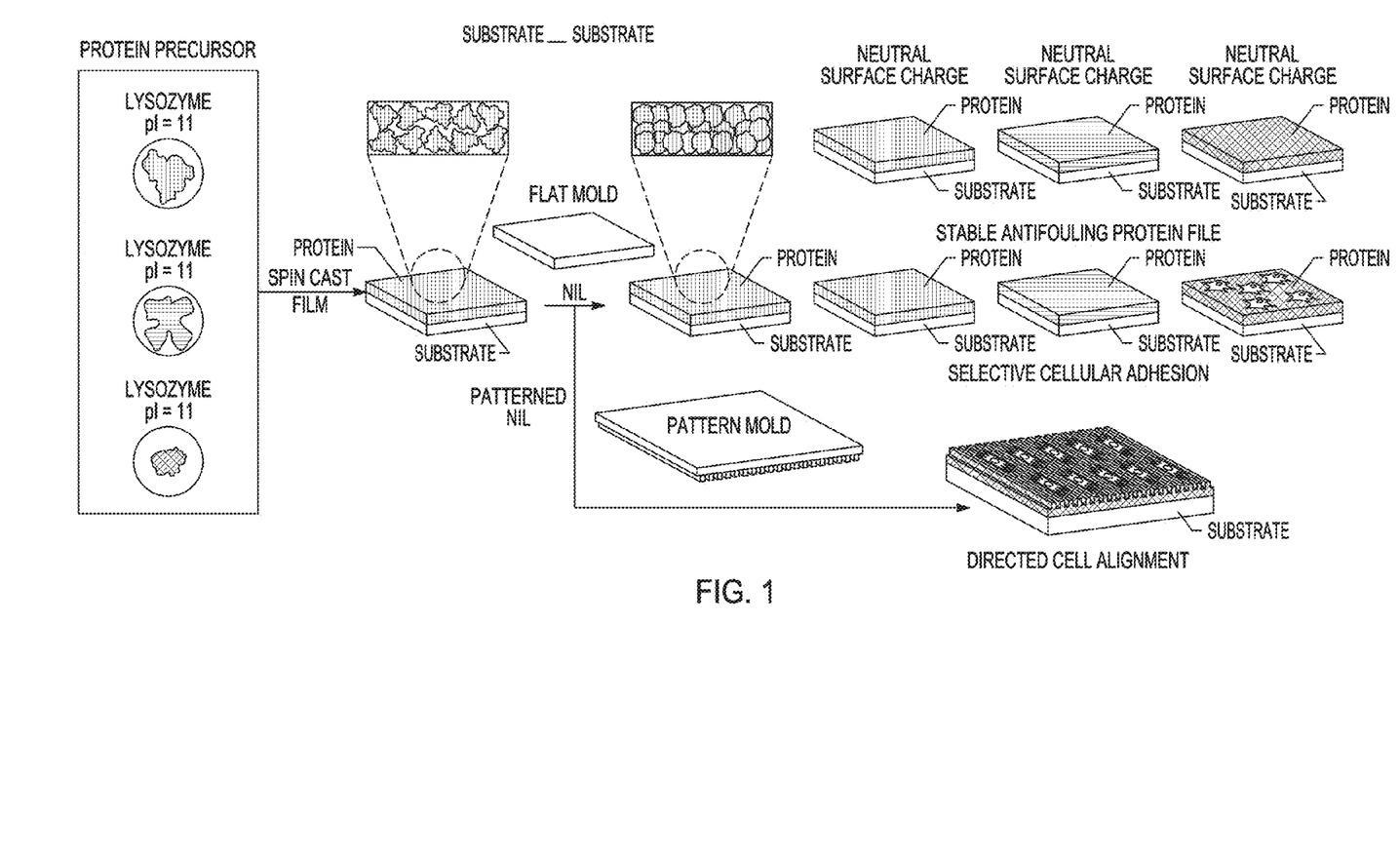
FIG. 1 illustrates a method for making imprinted protein films, in accordance with various embodiments.
Figure 2A:
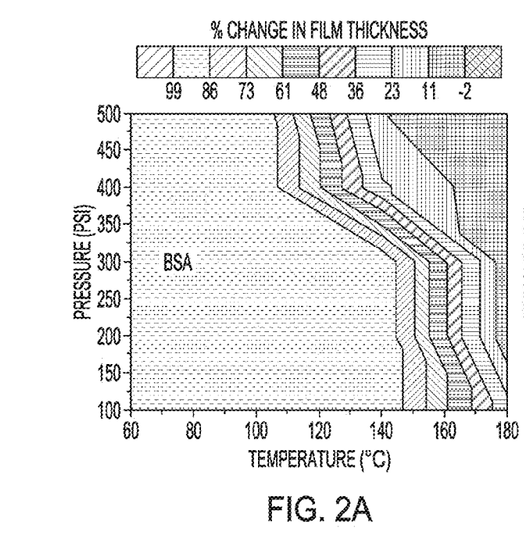
FIGS. 2A-2C illustrate the change in thickness of protein films formed using various imprinting conditions, in accordance with various embodiments.
Figure 2B:
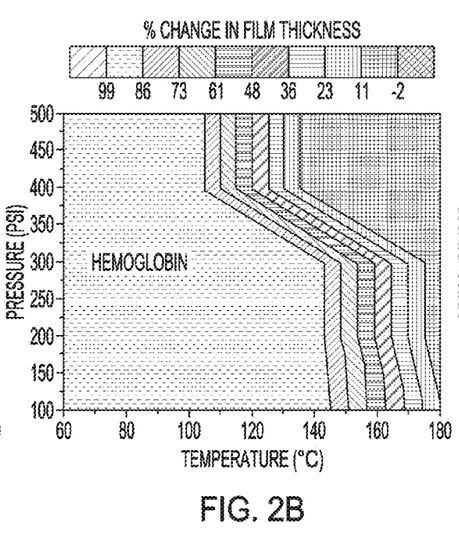
Figure 2C:
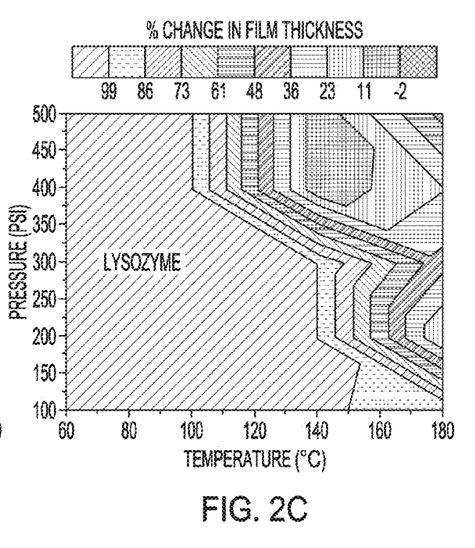

Precursor protein films were generated by spin casting 10% w/w aqueous solutions of protein onto plasma cleaned substrates. A general schematic of the method used is illustrated in FIG. 1. The films were about 200 nm in thickness as determined by ellipsometry and atomic force microscopy. The spin cast films were next imprinted/embossed using a fluorosilane-functionalized mold. The NIL conditions were parametrically varied to determine the factors influencing aqueous stability of the imprinted protein films, demonstrating that both pressure and heat are required for generating stable protein films. FIGS. 2A-2C illustrate the change in thickness of the films using various imprinting conditions, followed by washing for 1 min with water. The thickness was measured after drying using ellipsometry. While variation is observed in the pressure/temperature diagrams of the proteins, stable films could be generated from all three proteins at temperatures greater than 140° C. and pressures of 400 psi.

Example 2. Characterization of Films

Figure 3A:
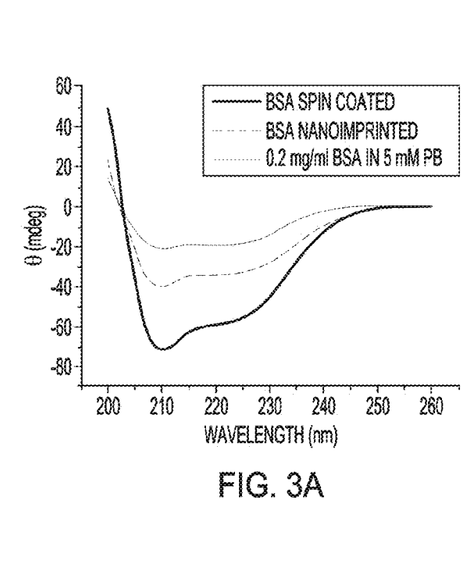
FIGS. 3A-3C illustrate circular dichroism (CD) spectra of various protein films, and of various proteins in phosphate buffer, in accordance with various embodiments.
Figure 3B:
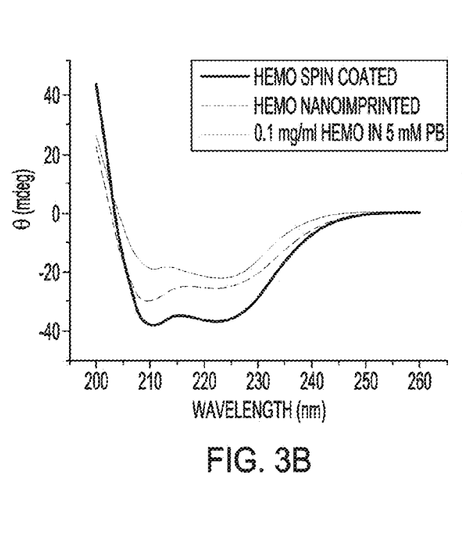
Figure 3C:
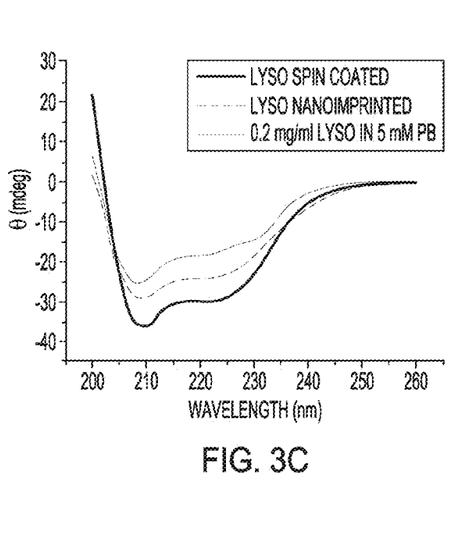

Thermal treatment can generate changes in protein structure. To assess the magnitude of these changes, the secondary structure of the individual protein components within the films was characterized using circular dichroism (CD) spectroscopy, with the results illustrated in FIGS. 3A-3C. The individual proteins in phosphate buffer are also shown for comparison. It is clear from the spectra that there is substantial retention of secondary structure, an important issue in translating protein properties to the resulting films. The lack of denaturation indicates that a more subtle mechanism of film stabilization is operative. Treatment of the films with 2-mercaptoethanol did not disrupt the films, ruling out inter-protein disulfide bonds as the stabilizing factor.

Figure 4:
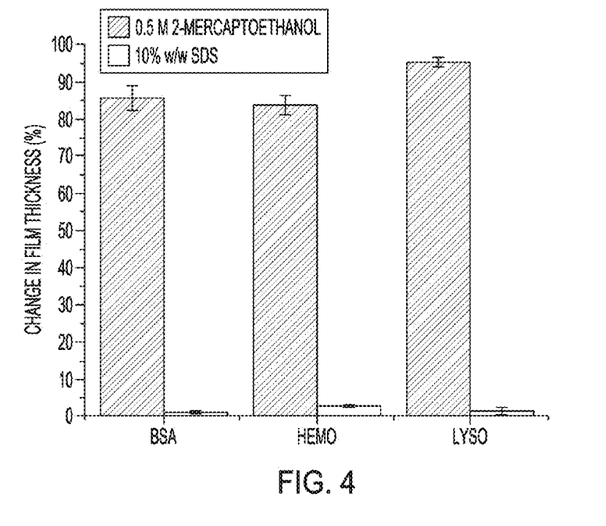
FIG. 4 illustrates the thickness change of various protein films after incubating with 0.5 M 2-mercaptoethanol and 10% sodium dodecyl sulfate (SDS) for 48 hours.

In contrast, treatment with surfactant (SDS) rapidly disrupted the films, suggesting that inter-protein hydrophobic interactions provide the observed stability of the film to aqueous media. FIG. 4 illustrates the thickness change of various protein films after incubating with 0.5 M 2-mercaptoethanol and 10% sodium dodecyl sulfate (SDS) for 48 hours. The thickness was measured by ellipsometry and the percentage changes were calculated by comparing the thicknesses of protein films before and after treating with 2-ME or SDS. SDS was used for disrupting hydrophobic interaction and 2-ME was able to break disulfide bonds of protein films. The results indicated that the protein films were stabilized mainly by hydrophobic interactions.

Example 3. Biocompatibility

Figure 3D:
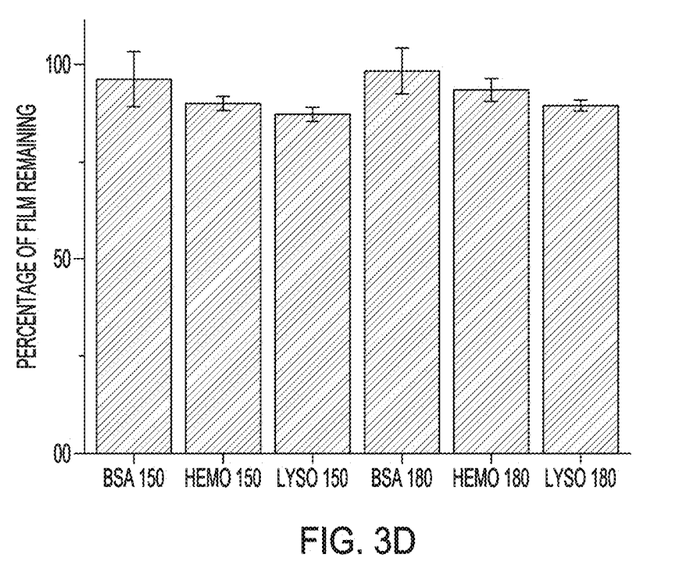
FIG. 3D illustrates the thickness change in various protein films after 48 hours of incubation in serum solution.
Figure 3E:
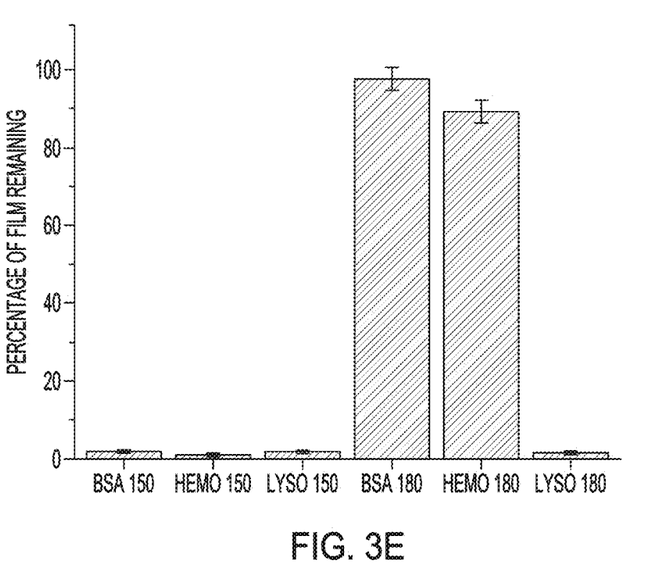
FIG. 3E illustrates the thickness change in various protein films incubation in trypsin solution.
Figure 3F:
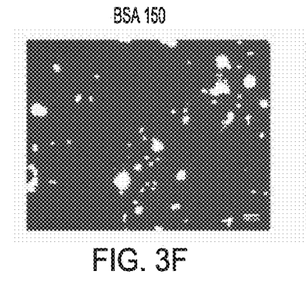
FIGS. 3F-3K illustrate fluorescence microscopy images of calcein-AM staining of adhered cells on various protein films after 24 hours. Scale bars are 100 μm.
Figure 3G:
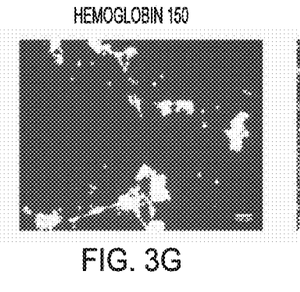
Figure 3H:
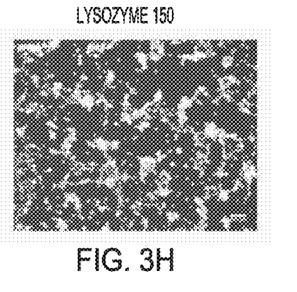
Figure 3I:
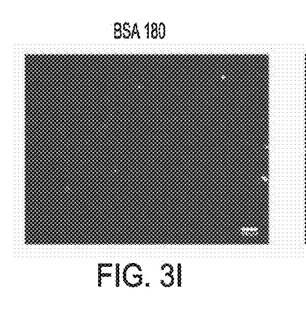
Figure 3J:
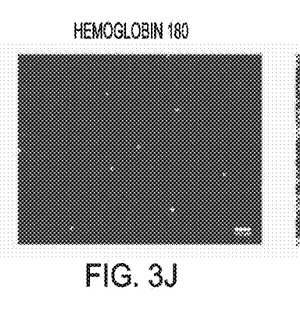
Figure 3K:
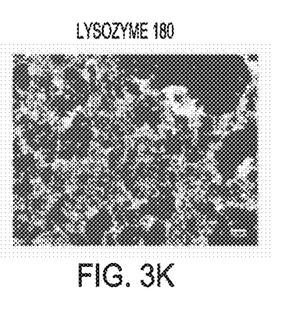

The potential utility of these materials as biomaterials was investigated. Resistance to protein fouling is an important requirement for both implantable devices and for ex vivo applications. A hypothesis was that the retention of protein structure in the imprinted films would result in the films conserving the non-aggregating properties of the proteins in solution. The biocompatibility of the films was evaluated by incubating films in 10% serum solutions for 48 hrs and then measuring the film thickness by ellipsometry. As shown in FIG. 3D, illustrating the thickness change of protein films measured by ellipsometry after 48 hours of incubation in 10% serum solution, there were no significant changes in film thickness, indicating films are both stable to serum conditions and resist non-specific protein adsorption. The response of the films to the intracellular protease trypsin was tested. After incubating in 0.01% trypsin solution for 24 hours, BSA and Hemo films fabricated at 180° C. were resistant to trypsin hydrolysis. All films imprinted at 150° C., however, were degraded (see, FIG. 3E, illustrating the thickness change in protein films measured by ellipsometry after 24 hours of incubation in 0.01% trypsin solution), making these films promising candidates for controlled release applications.

Figure 5A:
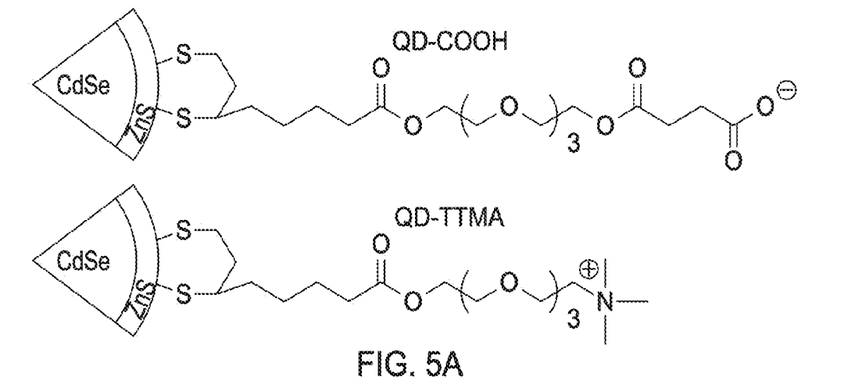
FIG. 5A illustrates chemical structures of surface functionalities on quantum dot probes, in accordance with various embodiments.
Figure 5B:
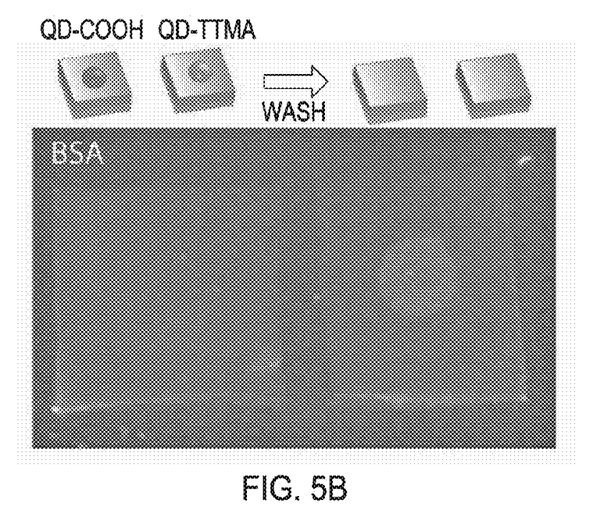
FIGS. 5B and 5C illustrate photographs of various protein films under UV irradiation after addition and incubation of a probe, before and after washing.
Figure 5C:
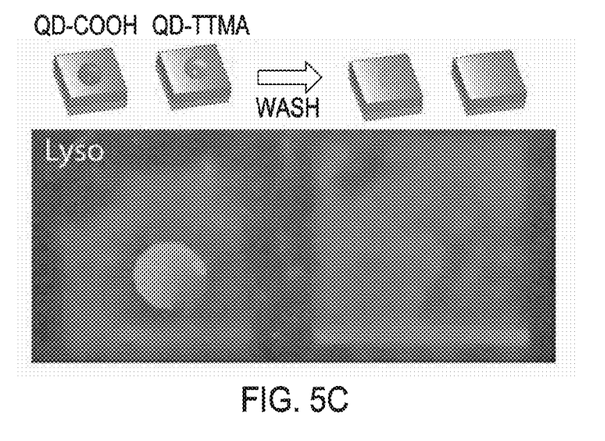

The retention of structure in the imprinted films suggested that the surfaces would manifest differing charges based on the precursor proteins. Preliminary evidence for this retention of charge was obtained through charge-selective adhesion of quantum dots (QDs), demonstrating that Lyso generated cationic films and BSA generated anionic films. FIG. 5A illustrates chemical structures of surface functionalities on the QDs. The charged QDs were used as probes for the surface charges of protein films by interacting with protein films through electrostatic interaction. 10 µL, 1 µM QD probes were dropped on the protein films and incubated for 15 mins in a humid chamber to avoid drying. After incubation, the protein films were washed by MILLI-Q water 5 times. FIGS. 5B and 5C illustrate photographs of BSA and Lyso protein films under UV irradiation after addition and incubation of the probe, before and after washing. Then the surface charges of protein films were determined by the fluorescent responses under the irradiation of a UV lamp at 365 nm. For the BSA film, only the positively charged probe showed a strong interaction, indicating that BSA film is negatively charged. The Lyso film showed the opposite result due to its inherent positive charge.

Functional demonstration of film differences was obtained through cell adhesion studies. NIH3T3 fibroblast cells were seeded onto protein films for 48 hrs, fixed, and stained with calcein-AM. Fluorescence microscopy images (see, FIGS. 3F-3K, illustrating fluorescence microscopy images of calcein-AM staining of adhered cells on protein films after 24 hours, with scale bars of 100 µm) show that films made from negatively charged BSA and neutral Hemo cells had limited adhesion on films fabricated at 150° C. while the films fabricated at 180° C. demonstrated no adhesion. In contrast, Lyso films provided excellent adhesion at both processing temperatures, consistent with the expected higher cell adhesion by the cationic surface.

Example 4. Nanoscale Patterning and Cellular Alignment

Figure 6A:
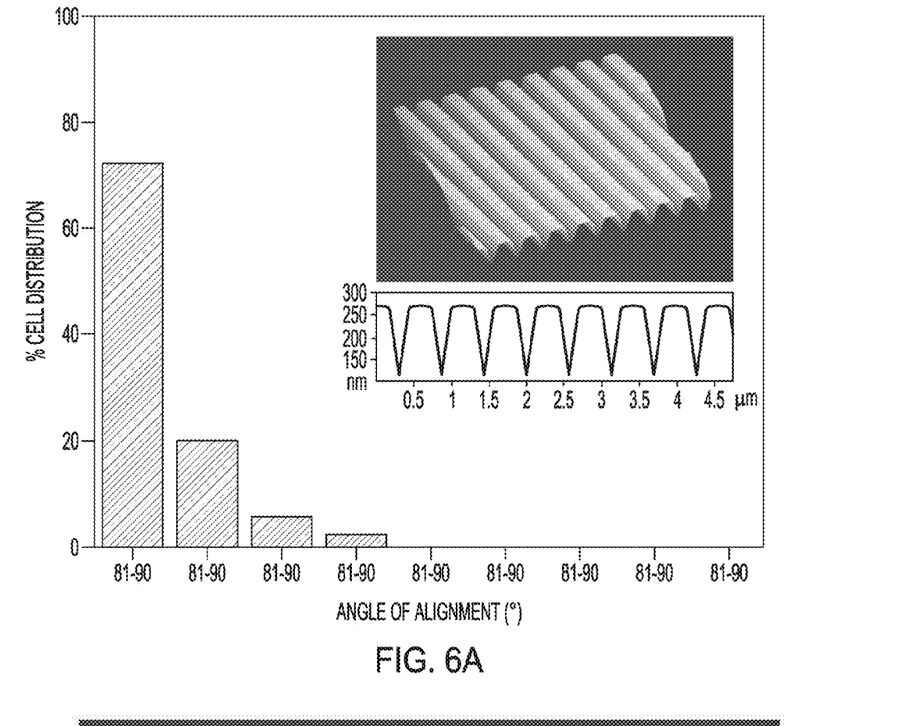
FIG. 6A illustrates the proportion of cells aligned along an imprinted pattern in a protein film, with the inset showing a 3D-atomic force microscopy image of the protein film including the pattern, in accordance with various embodiments.
Figure 6B:
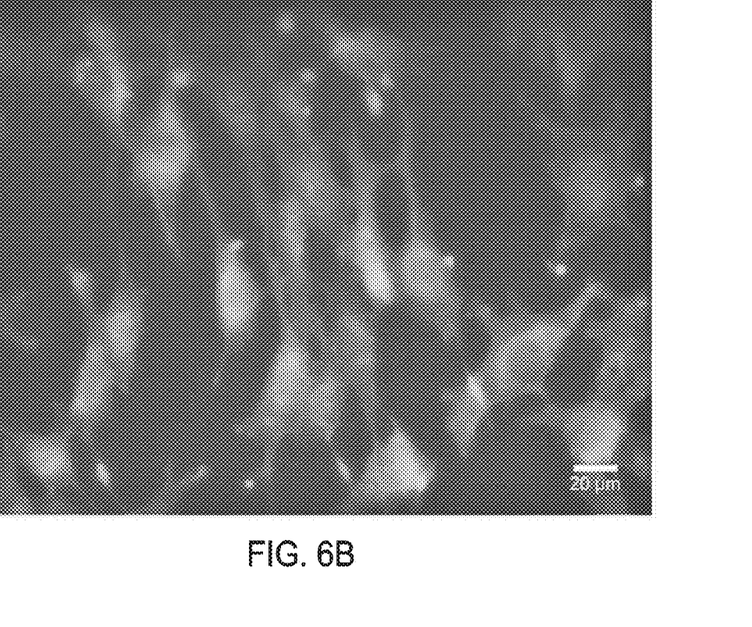
FIG. 6B illustrates a fluorescence micrograph of fibroblast cells cultured on a patterned protein film, in accordance with various embodiments.

The NIL process provides direct access to nanoscale pattering that can be used to dictate cellular alignment. Based on the cellular adhesion studies, Lyso was chosen to investigate cell alignment based on nanopatterning. Alignments were measured using microscopy. As shown in FIG. 6A inset, a 3D-atomic force microscopy image of the lysozyme film generated with a patterned mold, the Lyso film was texturally patterned using a 300 nm grooved pattern on the master mold. FIG. 6A illustrates the percentage of cells aligned along the imprinted pattern, showing that a majority of the cells aligned with the nanoscale pattern, demonstrating that film properties and patterning can be used together to effectively direct cellular growth. Next, NIH3T3 fibroblast cells were then cultured onto the patterned film. The cells were fixed, and Hoechst stain was used to stain cell nuclei and phalloidin was used to stain actin filaments. FIG. 6B illustrates a fluorescence micrograph of fibroblast cells cultured on a patterned protein film, in accordance with various embodiments.

Examples 1-4 demonstrate that the controlled heat and pressure provided by thermal NIL can be used to generate water-stable films from a range of precursor proteins. These films are generated without additives and retain substantial native protein structure, rendering them biocompatible and resistant to protein fouling. The films also retain physical properties of the precursor proteins, allowing surface charge and stability to be tuned by choice of precursor protein and processing conditions. Taken together, these films provide biocompatibility and sustainability that makes them promising for applications in biomaterials and beyond.

Example 5. Use of Pressure Reactor to Form Protein Films

To stabilize protein films on three-dimensional substrates, such as a catheter or stent, the use of a pressure reactor was investigated to provide pressure and heat for stabilizing protein films.

The pressure reactor equipment was purchased from High Pressure Equipment Company (PA, USA). The pressure reactor included a heating plate and a chamber filled with gas. A precursor film was generated using BSA as described in Example 1. A pressure of 400 psi was generated by $CO_2$ and the temperature of chamber was heated to 165° C. for 5 minutes, then the pressure reactor was allowed to cool.

Figure 7:
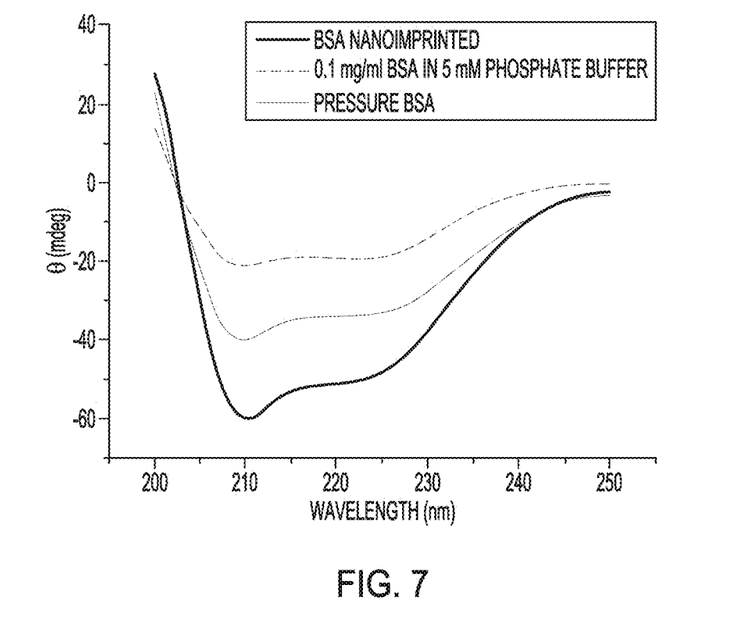
FIG. 7 illustrates circular dichroism (CD) spectra of protein film made using various techniques, and of the protein used to make the films in a phosphate buffer, in accordance with various embodiments.

FIG. 7 illustrates circular dichroism spectra of BSA films stabilized by NIL (BSA Nanoimprinted) and pressure reactor (Pressure BSA). The BSA in phosphate buffer is also shown for comparison. The circular dichroism spectra indicated that after pressure reactor treatment, the BSA film was stable and had a preserved secondary structures, which was similar to what was observed using the NIL technique.

Figure 8:
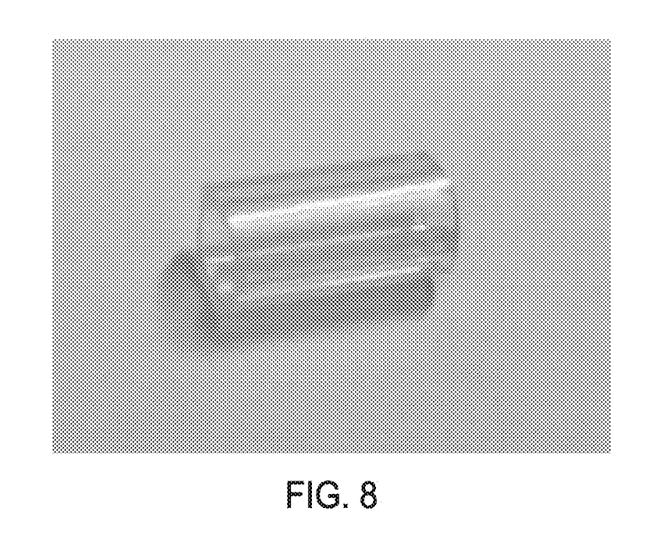
FIG. 8 illustrates a catheter coated with a hemoglobin film, in accordance with various embodiments.

The same technique was followed using hemoglobin with the pressure reactor, wherein the hemoglobin precursor solution was formed on a catheter. A photograph of the catheter after the pressure treatment is shown in FIG. 8. A brown color was visible on the catheter surface, which indicated successful coating of a hemoglobin film on catheter.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method of making a protein film, the method comprising:
placing on a substrate a protein solution comprising one or more proteins, to form a precursor protein film;
compressing the precursor protein film, to form a protein film.

Embodiment 2 provides the method of Embodiment 1, wherein the precursor protein film is about 1 nm to about 100 microns thick.

Embodiment 3 provides the method of any one of Embodiments 1-2, wherein the precursor protein film is about 100 nm to about 300 nm thick.

Embodiment 4 provides the method of any one of Embodiments 1-3, wherein the placing comprises printing, dipping, brushing, soaking, immersion, spraying, spin casting, or a combination thereof.

Embodiment 5 provides the method of any one of Embodiments 1-4, wherein the placing comprises offset printing, screen printing, flexographic printing, inkjet printing, laser printing, dot matrix printing, daisy wheel printing, pad printing, relief printing, rotogravure printing, gravure printing, jet printing, ultrasonic spray printing, piezoelectric printing, spin casting, three dimensional (3D) printing, or a combination thereof.

Embodiment 6 provides the method of any one of Embodiments 1-5, wherein the placing comprises spin casting.

Embodiment 7 provides the method of any one of Embodiments 1-6, wherein the substrate is a plasma-cleaned substrate.

Embodiment 8 provides the method of any one of Embodiments 1-7, wherein the protein solution is an aqueous protein solution.

Embodiment 9 provides the method of any one of Embodiments 1-8, wherein the protein solution is about 0.01 wt % to about 99.9 wt % protein.

Embodiment 10 provides the method of any one of Embodiments 1-9, wherein the protein solution is about 1 wt % to about 20 wt % protein.

Embodiment 11 provides the method of any one of Embodiments 1-10, wherein the protein is at least one of a fibrous protein, a globular protein, a transmembrane transport protein, a hormone or growth factor protein, a receptor protein, a DNA-binding protein, a transcription regulation protein, an immune system protein, a nutrient storage or transport protein, a chaperone protein, and an enzyme.

Embodiment 12 provides the method of any one of Embodiments 1-11, wherein the protein is at least one of anionic bovine serum albumin, neutral hemoglobin, and cationic lysozyme.

Embodiment 13 provides the method of any one of Embodiments 1-12, wherein compressing the precursor protein film is performed at a temperature of about −50° C. to about 500° C.

Embodiment 14 provides the method of any one of Embodiments 1-13, wherein compressing the precursor protein film is performed at a temperature of about 50° C. to about 250° C.

Embodiment 15 provides the method of any one of Embodiments 1-14, wherein compressing the precursor protein film is performed at a pressure of about 14 psi to about 20,000 psi.

Embodiment 16 provides the method of any one of Embodiments 1-15, wherein compressing the precursor protein film is performed at a pressure of about 200 psi to about 800 psi.

Embodiment 17 provides the method of any one of Embodiments 1-16, wherein compressing the protein film comprises compressing the protein film using a pressure vessel.

Embodiment 18 provides the method of any one of Embodiments 1-17, wherein compressing the protein film comprises compressing the protein film using a pressure reactor.

Embodiment 19 provides the method of any one of Embodiments 1-18, wherein compressing the protein film comprises pressing the protein film with a mold.

Embodiment 20 provides the method of Embodiment 19, wherein the mold comprises at least one of a fluorosilane-functionalized or a polydimethylsiloxane mold.

Embodiment 21 provides the method of any one of Embodiments 19-20 wherein pressing the precursor film with the mold comprises at least one of imprinting and embossing.

Embodiment 22 provides the method of any one of Embodiments 19-21 wherein pressing the precursor film with a mold comprises nanoimprint lithography.

Embodiment 23 provides the method of any one of Embodiments 19-22, wherein pressing the precursor film with a mold comprises patterned nanoimprint lithography.

Embodiment 24 provides the method of any one of Embodiments 1-23, wherein the substrate comprises at least one of a silica wafer, glass, quartz, a polydimethylsiloxane, and a polyester.

Embodiment 25 provides the method of any one of Embodiments 1-24, wherein compressing the precursor protein film forms a pattern.

Embodiment 26 provides the method of any one of Embodiments 1-25, wherein the protein film is about 1 nm to about 100 microns thick.

Embodiment 27 provides the method of any one of Embodiments 1-26, wherein the protein film is about 100 nm to about 300 nm thick.

Embodiment 28 provides the method of any one of Embodiments 1-27, further comprising washing the protein film.

Embodiment 29 provides the method of any one of Embodiments 1-28, further comprising at least partially removing the protein film from the substrate.

Embodiment 30 provides the method of any one of Embodiments 1-29, further comprising growing cells on the protein film.

Embodiment 31 provides the method of Embodiment 30, wherein the cells grown on the protein film substantially align with a pattern formed by the compressing of the precursor protein film.

Embodiment 32 provides the method of any one of Embodiments 1-31, wherein the protein film is substantially water-stable.

Embodiment 33 provides the method of any one of Embodiments 1-32, wherein the protein film is substantially biocompatible.

Embodiment 34 provides the method of any one of Embodiments 1-33, wherein the protein film is substantially resistant to degradation in a solution comprising serum.

Embodiment 35 provides the method of any one of Embodiments 1-34, wherein the protein film is substantially resistant to protein adsorption.

Embodiment 36 provides the method of any one of Embodiments 1-35, wherein the protein film is substantially resistant to protein fouling.

Embodiment 37 provides the method of any one of Embodiments 1-36, wherein the protein film is substantially resistant to microbial growth thereon.

Embodiment 38 provides the method of any one of Embodiments 1-37, wherein the protein film is substantially resistant to hydrolysis.

Embodiment 39 provides the method of any one of Embodiments 1-38, wherein the protein solution further comprises one or more components for release upon degradation of the film.

Embodiment 40 provides the method of any one of Embodiments 1-39, wherein the protein film retains at least some of the physical properties of proteins in the protein solution.

Embodiment 41 provides the method of any one of Embodiments 1-40, wherein the protein film substantially retains the secondary structure of proteins in the protein solution.

Embodiment 42 provides the method of any one of Embodiments 1-41, wherein the protein film comprises a surface comprising one or more charges that correspond to the one or more precursor proteins.

Embodiment 43 provides a protein film made by the method of any one of Embodiments 1-42.

Embodiment 44 provides a protein film comprising: one or more proteins that at least partially retain their secondary structure in the film, wherein the protein film comprises intermolecular hydrophobic interactions between the proteins.

Embodiment 45 provides the protein film of Embodiment 44, wherein the film is substantially water-stable.

Embodiment 46 provides the protein film of any one of Embodiments 44-45, wherein the film is substantially biocompatible.

Embodiment 47 provides the protein film of any one of Embodiments 44-46, wherein the film is substantially resistant to degradation in a solution comprising serum.

Embodiment 48 provides the protein film of any one of Embodiments 44-47, wherein the film is substantially resistant to protein adsorption.

Embodiment 49 provides the protein film of any one of Embodiments 44-48, wherein the film is substantially resistant to protein fouling.

Embodiment 50 provides the protein film of any one of Embodiments 44-49, wherein the film is substantially resistant to hydrolysis.

Embodiment 51 provides the protein film of any one of Embodiments 44-50, further comprising cells thereon.

Embodiment 52 provides the protein film of Embodiment 51, wherein the cells are substantially aligned with a pattern on the protein film.

Embodiment 48 provides the method or film of any one or any combination of Embodiments 1-47 optionally configured such that all elements or options recited are available to use or select from.

What is claimed is:

1. A method of making a protein film, the method comprising:
    placing on a substrate a protein solution comprising a protein, to form a precursor protein film; and
    compressing the precursor protein film, to form a protein film;
    wherein compressing the precursor protein film is performed at a pressure of about 14 psi to about 400 psi and at a temperature of about 135° C. to about 180° C., the protein film substantially retains the secondary structure of at least one of the proteins in the protein solution, and the protein is an anionic bovine serum albumin, a neutral hemoglobin, a cationic lysozyme, or a combination thereof.

2. The method of claim 1, wherein the precursor protein film is about 1 nm to about 100 microns thick.

3. The method of claim 1, wherein the placing comprises printing, dipping, brushing, soaking, immersion, spraying, spin casting, or a combination thereof.

4. The method of claim 1, wherein the protein solution is an aqueous protein solution, wherein the protein is about 1 wt % to about 20 wt % of the protein solution.

5. The method of claim 1, wherein compressing the protein film comprises compressing the protein film using a pressure vessel.

6. The method of claim 1, wherein compressing the protein film comprises pressing the protein film with a mold.

7. The method of claim 6 wherein pressing the precursor film with a mold comprises nanoimprint lithography.

8. The method of claim 1, wherein the substrate comprises a silica wafer, glass, quartz, a polydimethylsiloxane, a polyester, or a combination thereof.

9. The method of claim 1, wherein compressing the precursor protein film forms a pattern.

10. The method of claim 1, wherein the protein film is about 1 nm to about 100 microns thick.

11. The method of claim 1, further comprising at least partially removing the protein film from the substrate.

12. The method of claim 1, further comprising growing cells on the protein film.

13. The method of claim 12, wherein the cells grown on the protein film substantially align with a pattern formed by the compressing of the precursor protein film.

14. The method of claim 1, wherein the protein solution further comprises one or more components for release upon degradation of the film.

15. The method of claim 1, wherein the temperature during compression is from about 140° C. to about 165° C.

16. The method of claim 1, wherein the pressure during compression is from about 60 psi to about 400 psi.

* * * * *

UNITED STATES PATENT AND TRADEMARK OFFICE
CERTIFICATE OF CORRECTION

PATENT NO. : 10,073,340 B2  
APPLICATION NO. : 14/873540  
DATED : September 11, 2018  
INVENTOR(S) : Rotello et al.

Page 1 of 1

It is certified that error appears in the above-identified patent and that said Letters Patent is hereby corrected as shown below:

On the Title Page

In item (72), in "Inventors", in Column 1, Line 4, delete "(US);" and insert --(KR);-- therefor Signed and Sealed this  
Twenty-first Day of April, 2020

Andrei Iancu  
*Director of the United States Patent and Trademark Office*